(12) United States Patent
Blancke et al.

(10) Patent No.: US 10,265,473 B2
(45) Date of Patent: Apr. 23, 2019

(54) HOUSING OF A DRUG DELIVERY DEVICE

(71) Applicant: Sanofi-Aventis Deutschland GmbH, Frankfurt am Main (DE)

(72) Inventors: Stefan Blancke, Frankfurt am Main (DE); Axel Teucher, Frankfurt am Main (DE); Michael Jugl, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 214 days.

(21) Appl. No.: 15/100,369

(22) PCT Filed: Dec. 8, 2014

(86) PCT No.: PCT/EP2014/076811
§ 371 (c)(1),
(2) Date: Sep. 6, 2016

(87) PCT Pub. No.: WO2015/086482
PCT Pub. Date: Jun. 18, 2015

(65) Prior Publication Data
US 2016/0296701 A1 Oct. 13, 2016

(30) Foreign Application Priority Data

Dec. 11, 2013 (EP) .................................... 13196576

(51) Int. Cl.
*A61M 5/24* (2006.01)
*A61M 5/315* (2006.01)
(Continued)

(52) U.S. Cl.
CPC ............ *A61M 5/24* (2013.01); *A61M 5/2459* (2013.01); *A61M 5/28* (2013.01); *A61M 5/3155* (2013.01);
(Continued)

(58) Field of Classification Search
CPC .. A61M 2005/2407; A61M 2005/2433; A61M 2005/2462; A61M 2005/2485;
(Continued)

(56) References Cited

U.S. PATENT DOCUMENTS

2011/0046566 A1* 2/2011 Elahi ................... A61M 5/3129
604/214
2012/0265136 A1 10/2012 Lawlis et al.
(Continued)

FOREIGN PATENT DOCUMENTS

WO WO2008/062025 5/2008
WO WO2008/074897 6/2008
(Continued)

OTHER PUBLICATIONS

International Search Report and Written Opinion in International Application No. PCT/EP2014/076811, dated Jan. 19, 2015, 8 pages.
(Continued)

*Primary Examiner* — Quynh-Nhu H. Vu
(74) *Attorney, Agent, or Firm* — Fish & Richardson P.C.

(57) ABSTRACT

The present invention relates to a housing of a drug delivery device comprising a cylindrically shaped body (12) to accommodate a drive mechanism (13) and comprising a cartridge holder (14) to accommodate a cartridge (16) containing a dispensable medicament, the housing further comprising a connector assembly (20) to releasably interconnect body (12) and cartridge holder (14), the connector assembly (20) comprising: a tangentially extending recessed structure (30) with a tangential opening (31) to receive a radially extending pin (26), wherein the recessed structure (30) is fastened to one of body (12) and cartridge holder (14) and wherein the pin (26) is fastened to the other one of body (12) and cartridge holder (14), a release member (40) having a retaining portion (42) to cover the opening (31) in a locking
(Continued)

configuration (60), wherein the release member (40) is displaceable in tangential direction (3) against a restoring force away from the recessed structure (30) into a release configuration (62), in which the opening (31) is uncovered to tangentially remove the pin (26) therefrom.

16 Claims, 5 Drawing Sheets

(51) Int. Cl.
*A61M 5/32* (2006.01)
*A61M 5/28* (2006.01)

(52) U.S. Cl.
CPC ............ *A61M 5/3158* (2013.01); *A61M 5/32* (2013.01); *A61M 5/3286* (2013.01); *A61M 2005/2407* (2013.01); *A61M 2005/2433* (2013.01); *A61M 2005/2462* (2013.01); *A61M 2005/2485* (2013.01); *A61M 2005/2488* (2013.01)

(58) Field of Classification Search
CPC ............ A61M 2005/2488; A61M 5/24; A61M 5/2459; A61M 5/28; A61M 5/3155; A61M 5/3158; A61M 5/32; A61M 5/3286
See application file for complete search history.

(56) References Cited

U.S. PATENT DOCUMENTS

| | | | | |
|---|---|---|---|---|
| 2013/0030383 | A1 | 1/2013 | Keitel | |
| 2013/0068319 | A1* | 3/2013 | Plumptre | A61M 5/24 137/315.01 |
| 2013/0211327 | A1* | 8/2013 | Osman | A61M 5/24 604/111 |
| 2014/0052075 | A1* | 2/2014 | Schneider | A61M 5/24 604/207 |

FOREIGN PATENT DOCUMENTS

| | | |
|---|---|---|
| WO | WO2011/089207 | 7/2011 |
| WO | WO2012/020084 | 2/2012 |
| WO | WO2012/152666 | 11/2012 |

OTHER PUBLICATIONS

International Preliminary Report on Patentability in International Application No. PCT/EP2014/076811, dated Jun. 14, 2016, 5 pages.
Rote Liste, "50. Hypophysen-, Hypothalamushormone, andere regulatorische Peptide u. ihre Hemmstoffe," Chapter 50, ed. 2008, 20 pages.

* cited by examiner

HOUSING OF A DRUG DELIVERY DEVICE

CROSS-REFERENCE TO RELATED APPLICATIONS

This application is a U.S. national stage application under 35 USC § 371 of International Application No. PCT/EP2014/076811, filed on Dec. 8, 2014, which claims priority to European Patent Application No. 13196576.6, filed on Dec. 11, 2013, the entire contents of which are incorporated herein by reference.

The present invention relates to a housing of a drug delivery device and to a respective drug delivery device. In particular, the invention relates to an injection device such like a pen-type injector operable to repeatedly dispense numerous doses of an injectable medicament.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod, which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In order to provide access to an empty cartridge the housing of the drug delivery device has to be opened or disassembled. One approach to replace an empty cartridge by a new one is to make use of a housing comprising at least two mutually detachable components, e.g. a body and a cartridge holder. Typically, the body serves to accommodate the drive mechanism comprising all those mechanically interacting components of the drug delivery device that are necessary to displace a piston rod in a distal, hence in a dispensing direction, in order to expel a medicament from the cartridge. A second housing component releasably interconnectable with the body typically serves as a cartridge holder. The cartridge holder is designed to receive and to accommodate the cartridge filled with the medicament to be dispensed.

Typically, the cartridge holder features at least one transparent inspection window allowing to visually inspect the filling level of the cartridge. Moreover, the distal end of such a cartridge holder is typically equipped with a standardized connector to releasably engage with a piercing assembly, e.g. a double-tipped needle. By attaching or engaging the piercing assembly with the cartridge holder, a proximally extending needle portion may extend through a distal opening of the cartridge holder so as to penetrate and to pierce a seal located at a distal end of the cartridge. By attaching the needle assembly to the cartridge holder a fluid transferring access to the interior of the cartridge can be established.

Cartridge holder and body can be releasably connected in many different ways. Document EP 2 121 086 B1 discloses a medical delivery system comprising a locking ring with L-shaped grooves. This medical delivery system comprises a container and a dosing assembly adapted to be fastened to the container, wherein one of the dosing assembly and the container defines a first part having at least one projection which during fastening of the container to the dosing assembly is adapted to be received in or by at least one corresponding groove or projection of a second part which is defined by the other one of the dosing assembly and the container. There, the first part comprises a fixed part and a rotatable element defining at least one of said projection and/or groove, which during fastening of the container to the dosing assembly is adapted to be received in or by at least one of said corresponding groove and/or projection of the second part.

Certain aspects of the disclosure can be implemented to provide a smooth operating, long lasting and intuitively operable connector assembly for releasably connecting a proximal body and a distal cartridge holder of a drug delivery device's housing. The connector assembly should feature a minimum of mechanically interacting components. It should be intuitive and easy in handling and should further allow and support an easy, cost efficient and straightforward assembly during a manufacturing process of the drug delivery device.

SUMMARY OF THE INVENTION

In a first aspect a housing of a drug delivery device is provided. The housing comprises a cylindrically or tubular-shaped body to accommodate a drive mechanism. The housing further comprises a cartridge holder, which is also cylindrically-shaped and which is to be releasably interconnected with the body. The cartridge holder is adapted and designed to accommodate a cartridge containing a dispensable medicament. The cartridge holder is designed to removably receive a cartridge featuring a cylindrical barrel of vitreous material that is plugged or sealed by a piston at a proximal end facing towards a piston rod of the drive mechanism extending in longitudinal or axial direction with regard to the cylindrical shape of the housing.

The housing further comprises a connector assembly to releasably interconnect body and cartridge holder. The connector assembly comprises a tangentially extending recessed structure with a tangential opening, i.e. an opening, which is accessible from the tangential direction. Said recessed structure is adapted to receive a radially extending pin. The recessed structure if fastened to one of body and cartridge holder while the pin is fastened to the other one of body and cartridge holder.

The connector assembly further comprises a release member having a retaining portion to cover, to close or to obstruct the recessed structure's opening in a locking configuration. At least the release member is displaceable in tangential direction against a restoring force and away from the recessed structure into a release configuration. In the release configuration the retaining portion no longer closes or obstructs but uncovers and reveals the recessed structure's opening in order to allow and support tangential removal of the pin therefrom.

In an embodiment the pin is located at a proximal end portion of the cartridge holder and extends radially outwardly while the release member is located and arranged at a distal end portion of the body, which is adapted to at least partially receive the proximal end of the cartridge holder. In this way, the cartridge holder can be at least partially inserted into the body in such a way, that the connector assembly's recessed structure engages with the at least one pin of the cartridge holder. Since the recessed structure with the pin located therein extends in tangential direction and is open in tangential direction the recessed structure provides an axially acting fixing means for the pin. Typically, the recessed structure features a tangentially extending indentation, into which the cartridge holder's is insertable.

In the locking configuration the pin is typically tangentially sandwiched between the recessed structure and the retaining portion of the release member, which may directly abut with the recessed structure. The size and geometry of the recessed structure is selected such that it accommodates at least the pin. In the locking configuration the pin is axially secured by the tangentially extending recessed structure and is hindered from leaving the recessed structure in tangential direction by the retaining portion.

For releasing the connector assembly, hence for transferring the connector assembly from the locking configuration into the release configuration it is intended to displace the release member in tangential direction so as to liberate the pin in the recessed structure. By displacing the release member away from the recessed structure the retaining portion thereof no longer abuts with the recessed structure and the opening of the recessed structure is hence unobstructed. The pin may then be removed from the recessed structure, e.g. by a rotation of the cartridge holder relative to the body with regard to a rotation axis extending parallel or coinciding with a longitudinal axis of the housing, thereby displacing the at least one pin in tangential direction relative to the recessed structure.

Once the pin leaves the recessed structure in tangential direction it is also no longer constrained or fixed in axial or longitudinal direction. Consequently, the tangentially directed displacement of the release member allows and supports removal of the pin out of the recessed structure thereby enabling a mutual axial displacement of cartridge holder and body.

In general, the recessed structure may be integrally formed with or may be integrated into one of body or cartridge holder. Generally, the connector assembly only requires one displaceable component, which is displaceable relative to body and cartridge holder. In the event that the recessed structure is integrated into the body or cartridge holder it is sufficient that only the release member of the connector assembly is displaceable relative to the recessed structure. In this way a rather simple and cost efficient connector assembly for body and cartridge holder can be provided.

According to an embodiment the release member is rotatably or pivotally supported on one of body and cartridge holder with respect to a longitudinal axis of body or cartridge holder. A rotatable or pivoting motion of the release member relative to the body or cartridge holder allows to displace the retaining portion of the release member in tangential direction so as to liberate and to release the pin located in the recessed structure. In addition it is also conceivable, that the release member is also rotatable or pivotable in tangential direction for connecting or reconnecting of body and cartridge holder. Hence, by means of a tangentially directed displacement of the release member relative to the recessed structure a pin of the connector assembly may also be inserted into the recessed structure.

Typically, the release member is rotatably or pivotally located in a distal front face of the body or in a proximal front face of the cartridge holder in order to releasably engage with a proximal portion of the cartridge holder or with a distal portion of the body, respectively.

The release member may be axially or radially supported on one of body and cartridge holder. It is for instance conceivable, that the release member is axially rotatably supported on a bearing surface or on a bearing flange extending radially inwardly from a cylindrical sidewall of body or cartridge holder. It is also conceivable, that the release member is rotatably supported in the body or in the cartridge holder in such a way, that sidewall portions of body or cartridge holder completely or at least partially enclose the outer circumference of the release member. In this way the release member may be axially and circumferentially or radially secured and constrained to one of the body and the cartridge holder.

In another embodiment the release member comprises a ring structure. Here, the retaining portion interacting with the recessed structure of the connector assembly axially protrudes from the ring structure. The ring or annular structure of the release member is typically a closed ring but may also comprise only ring portions separated by at least one radially extending gap. By means of a ring structure a particular smooth rotatable or pivotable support of the release member can be provided. The release member may be supported on a flange-like and radially inwardly extending bearing surface of body or cartridge holder. By means of an annular ring structure a homogeneous and smooth mechanical support can be provided allowing and supporting a smooth, easy and well-defined rotation or pivoting behavior of a release member relative to one of body and cartridge holder.

In addition, the ring structure further supports an axially nested or interleaved configuration of cartridge holder and body. If the release member is for instance arranged at or in a distal receptacle of the body a proximal end portion of the cartridge holder comprising the at least one pin may extend into or even through the release member's ring structure. Hence, when arranged or attached to the body the release member with its ring structure may receive a proximal end portion of the cartridge holder. In another configuration, wherein the release member is attached to the cartridge holder it may receive a distal end portion of the body to be inserted into the cartridge holder. In either way the ring structure of the release member supports and allows for an axially and radially overlapping assembly of cartridge holder and body so as to provide a rather robust and stable housing of the drug delivery device.

According to another embodiment the release member comprises a radially extending radial stop to engage with a complementary or corresponding radial stop of one of body or cartridge holder. In this way the release member's tangential displacement towards the locking configuration can be delimited and stopped. Typically, the radial stop extends radially outwardly from the release member. It may be arranged at an axial, hence at a distal or proximal end of the retaining portion that axially protrudes from the ring structure.

A radially outwardly extending radial stop of the release member is beneficial for not obstructing the interior of the release member's ring structure. Moreover, by having mutually corresponding and directly inter-engaging radial stops of release member and at least one of body or cartridge holder a well-defined locking configuration of the release member relative to the body or cartridge holder can be defined. In this way it is even possible to at least temporally transfer the connector assembly from the locking configuration into the release configuration by displacing the recessed structure in tangential direction away from the release member. Due to the release member's radial stop being in engagement with a corresponding radial stop of one of body or cartridge holder the release member is hindered to follow a respective displacement of the recessed structure.

So transferring the connector assembly from the locking configuration into the release configuration may be conducted in at least two different ways. The release configuration may be obtained by tangentially displacing the release member while the recessed structure is fixed to one of body and cartridge holder or it may be obtained by displacing the recessed structure relative to the release member while the release member is fixed to one of body and cartridge holder.

Providing two different ways of transferring the connector assembly from a locking configuration into a release configuration is of particular benefit for connecting and disconnecting body and cartridge holder. For instance, during a connecting operation the release member may be fixed to one of body and cartridge holder while the recessed structure is displaceable against a restoring force. For disconnecting of cartridge holder and body the recessed structure may be fixed to one of body and cartridge holder while it is the release member which is displaceable in tangential direction relative to one of body and cartridge holder, hence relative to the recessed structure.

According to a further embodiment the release member is displaceable against the action of at least one tangentially extending or tangentially acting return spring. The return spring may comprise a compression spring extending in tangential direction so that the spring with one end engages with the release member and with another end engages with one of body and cartridge holder. Alternatively it is conceivable, that the return spring comprises a helical spring extending parallel to the cylindrically-shaped body or cartridge holder. Further alternatively the return spring may comprise a torsion spring of ring or disc-like shape featuring axially extending end portions to engage with the release member and with one of body and cartridge holder.

By means of a return spring, the release member is rotatable or pivotable with regard to the longitudinal axis from the locking configuration towards the release configuration against the action of the return spring. Hence, it is the at least one return spring that provides the restoring force against which the release member is displaceable in tangential direction.

According to a further embodiment the connector assembly also comprises a locking member rotatably or pivotably supported with respect to the longitudinal axis on that one of body and cartridge holder also supporting the release member. Here, the recessed structure to engage with the pin is a component of the locking member or is integrally formed with the locking member. By having the recessed structure located in or on a rotatable or pivotable locking member transferring of the connector assembly between the locking configuration and release configuration can be equally attained by displacing the locking member relative to the release member in circumferential or tangential direction. Release member and locking member are both located and pivotally or rotatably attached to one of the housing component's body or cartridge holder. Locking member and release member form a kind of a latch mechanism in order to catch and to retain the pin of the connector assembly in a well-defined locking configuration, in which the pin and hence one of body and cartridge holder featuring the pin remains fastened to one of body and cartridge holder featuring locking member and release member.

According to a further embodiment the release member and the locking member axially abut. Furthermore, one of release member and locking member is axially fixed to one of body and cartridge holder to axially constrain the other one of release member and the locking member in abutment with a bearing surface of one of body and cartridge holder. In this way, one of locking member and release member is axially fixed in the connector assembly, hence to one of body and cartridge holder by axially sandwiching the particular component between one of body and cartridge holder and the other one of release member and locking member.

For example the locking member may be axially supported by a bearing surface or by a radially extending flange of the body. In addition, the release member may be axially arranged in abutment with that axial side of the locking member that faces away from the bearing surface. By axially attaching or axially securing the release member to the body also the locking member is inherently axially constrained to the body but may be still rotatable relative to the body with regard to the longitudinal axis. In order to keep the locking member axially fixed to the body the release member may comprise at least one radially inwardly extending flange portion that axially abuts with e.g. a distally-facing surface of the locking member that may be of annular shape.

The release member may be positively engaged with the body, e.g. by way of a snap fit or by some additional component that serves to axially fix the release member to the body but allows and supports a rotation of the release member relative to the body. Depending on the specific arrangement and abutment of release member and locking member it is also conceivable, that it is the release member, which is axially sandwiched between the locking member and a bearing surface of one of body and cartridge holder. Then it is the locking member, which is axially but rotatably fixed to one of body and cartridge holder.

According to another embodiment the at least one return spring tangentially extends between the locking member and the release member to keep the retaining portion in abutment with the recessed structure. With this embodiment the return spring serves to displace the locking member relative to the release member and vice versa. The return spring may engage with one end or with a connecting portion with the locking member while another end or connecting portion is engaged with the release member. In this way, the return spring is operable to keep the tangential opening of the recessed structure effectively obstructed and closed by the retaining portion of the release member.

When the at least one return spring tangentially extends between the locking member and the release member it does not have to directly engage with one of body and cartridge holder. In this way, the return spring does not necessarily have to be assembled to one of cartridge holder and body. Instead, the return spring can be assembled between locking member and release member so that the connector assembly, the at least one return spring, the locking member as well as the release member can be preconfigured and preassembled before such a preassembly as a whole is to be attached and assembled to one of body and cartridge holder.

According to a further embodiment the locking member also comprises a ring structure. The recessed structure of the locking member axially protrudes from the ring structure in order to engage with the radially extending pin. If for example release member and locking member are arranged at or in a distal end of the body the recessed structure as well as the retaining portion both extend in distal direction from the respective ring structures, hence towards the cartridge holder featuring the radially outwardly extending pin to engage with the recessed structure. In this way, the ring structures of the locking member and the release member may substantially overlap or may mutually abut in radial and/or axial direction. In this way, a rather smooth and homogeneous mutual abutment of release member and locking member can be attained.

According to another embodiment the locking member also comprises a radially extending radial stop to engage with a complementary radial stop of one of body or cartridge holder to delimit a locking member's tangential displacement towards the locking configuration. In this way and by means of the radial stop the locking member can be kept in a locking configuration relative to one of body or cartridge holder while the release member may be rotatable against or under the action of the return spring. In this way, the locking member is hindered to follow a rotating or pivoting displacement of the release member when the retaining portion thereof is rotated in a direction so as to separate from the recessed structure.

According to another embodiment the release member comprises at least two tangentially separated retaining portions to releasably engage with at least two correspondingly-shaped and also tangentially separated recessed structures. In an embodiment wherein the recessed structures belong to the rotatable or pivotable locking member, release member as well as locking member may comprise geometrically oppositely located and symmetrically designed retaining portions and recessed structures. In addition, the at least two retaining portions and recessed structures may both feature radially extending stops so that a mechanical and spring biased abutment or engagement between release member and recessed structure can be equally distributed among the plurality of mutually abutting radial stops. In this way mechanical forces and point loads between inter-engaging stops can be limited, which is beneficial in terms of durability and robustness of the connector assembly and hence of the entire housing of the drug delivery device.

According to a further embodiment a free and axial end of at least one of recessed structure and retaining portion comprises a beveled edge. By means of a beveled edge a rotational or pivoting motion of at least one of release member and locking member can be induced by actually urging the pins of one of body and cartridge holder onto the beveled edge. The beveled edge is located at a radial position that coincides with the radial position and extension of the pin. In the event that several recessed structures and retaining portions are provided the connected assembly will also feature a corresponding number of pins located and arranged at respective radial positions to engage with the recessed structures.

By means of at least one beveled edge a purely translational displacement of one or several pins in axial, hence in distal or proximal direction can be transferred into a pivoting or rotation motion of at least one of release member and locking member. If the beveled edge is provided on or at the recessed structure, an end of the beveled edge extends into the tangentially extending recessed structure, hence in a tangentially extending slit or receptacle to receive the pin.

According to a further embodiment the connector assembly is transferable from the locking configuration into the release configuration by a tangential displacement of the locking member relative to the release member. This displacement, typically featuring a pivoting or rotating motion with regard to the longitudinal axis of the housing is induced or inducible by an axial displacement of the pin towards the release member, thereby engaging with the beveled edge. When having two or even more, e.g. equidistantly arranged recessed structures and retaining portions along the circumference of release member, one of body and cartridge holder or locking member, it is of particular benefit to have a corresponding number of beveled edges so that an axial displacement of various pins may equally contribute to a rather smooth rotational or pivoting displacement of either the release member or the locking member relative to each other and/or relative to one of body and cartridge holder.

In another aspect the invention equally applies to a drug delivery device comprising a housing as described above and further having a drive mechanism arranged in the body of the housing and comprising at least a piston rod to operably engage with a piston of a cartridge containing the medicament. Typically, the drug delivery device is designed as a pen-type injector either manually or automatically driven by an actuation force of a user or by means of some kind of mechanical or electrical energy source. The housing as well as the drive mechanism typically comprise numerous plastic components, in particular injection molded plastic components. Moreover, apart from the cartridge and e.g. a return spring or other spring elements the entire drug delivery device may comprise only or mainly injection molded plastic components allowing for a rather cost efficient mass manufacturing and mass production process.

According to another embodiment the drug delivery device is readily equipped with a replaceable cartridge that is filled with a medicament and which is arranged in the housing's cartridge holder.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, a brief description of the drawings is provided, in which.

DETAILED DESCRIPTION

Figure 1:
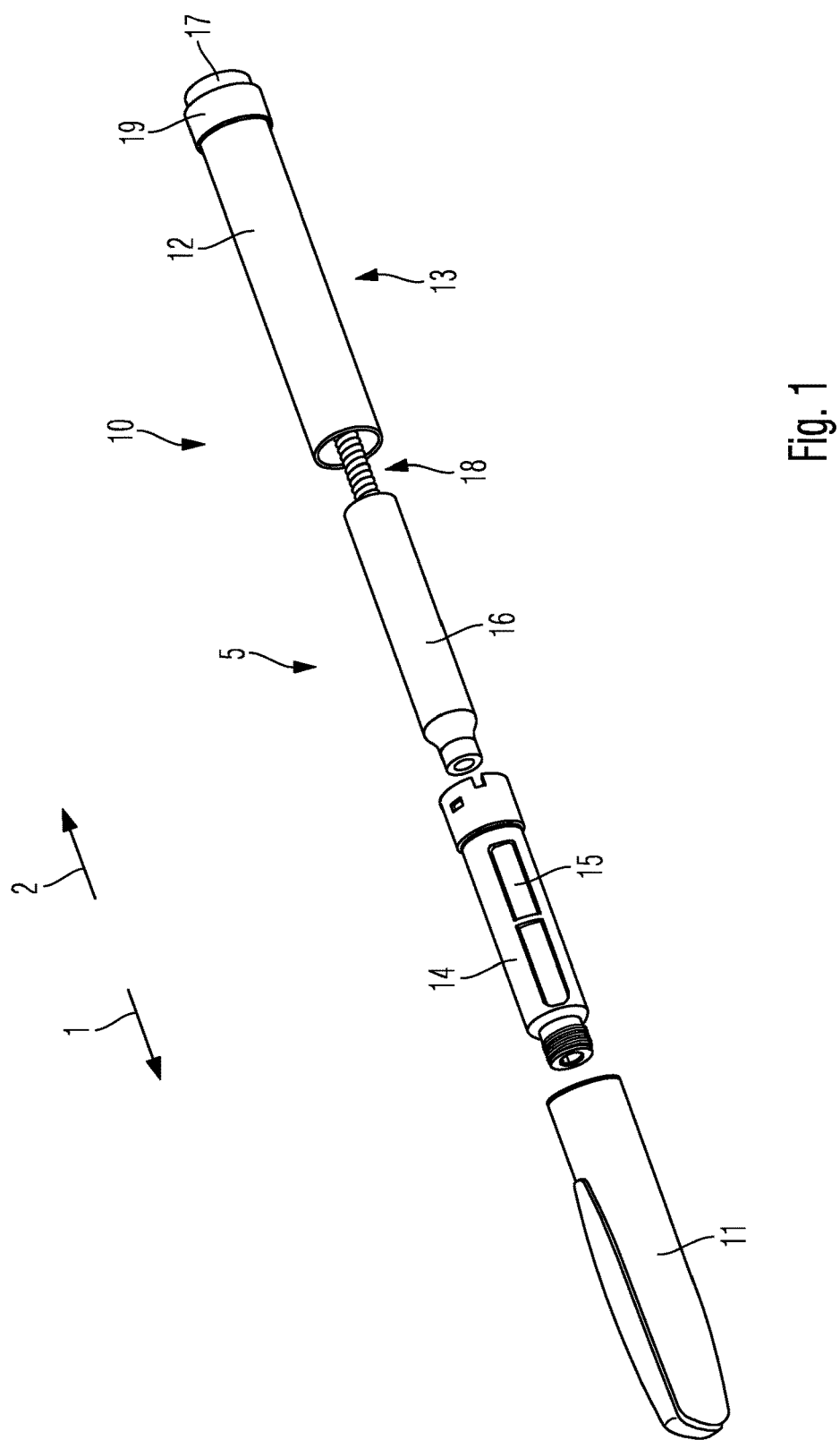
FIG. 1 shows a simplified and schematic exploded view of a drug delivery device.

The drug delivery device 5 as schematically illustrated in FIG. 1 is of pen injector-type. It comprises a housing 10 having a proximal portion denoted as body 12 and further having a distal portion denoted as cartridge holder 14. In addition the housing 10 further comprises a protective cap 11 to cover the cartridge holder 14 when the drug delivery device 5 is not in use. As can be seen from FIG. 1, the cartridge holder 14, hence the distal end of the drug delivery device 5 features a threaded socket to threadedly engage with a standardized piercing or injection assembly having a double-tipped needle.

Inside the cartridge holder 14 there is arranged a cartridge 16. The cartridge holder 14 comprises a window 15 to allow visual inspection of the cartridge located therein. Typical cartridges 16 comprise a vitreous barrel of tubular shape. In distal direction 1, hence at a distal end the cartridge 16 comprises a pierceable seal to be penetrated by the piercing assembly (not illustrated). Towards the proximal end the cartridge 16 is typically sealed by a piston which is displaceable in distal direction 1 under the effect of an advancing piston rod 18. In this way, a well-defined amount of medicament can be dispensed and expelled from the cartridge 16 on request. The drive mechanism 13 located in the body 12 typically features a dose setting and a dose dispensing mechanism.

At a proximal end of the body 12 there is provided a dose selector 19, which may be rotatable either clockwise or counter-clockwise to set a dose, i.e. to increase or to decrease a dose to be dispensed. In addition there is provided an actuation button 17 at the proximal end of the body. By depressing the actuation button 17 in distal direction an injection procedure may be triggered or executed, thereby advancing the piston rod 18 in distal direction 1 so as to expel a previously set dose of the medicament from the cartridge 16. The proximal direction 2 is facing away from the injection and distal end of the drug delivery device 5. Once the medicament contained in the cartridge 16 has been used up or if for some other reason the cartridge 16 has to be replaced disassembly of the housing 10 becomes necessary. For this, cartridge holder 14 and body 12 are interconnected by means of a connector assembly 20 which is shown in more detail in FIGS. 2-8.

Figure 2:
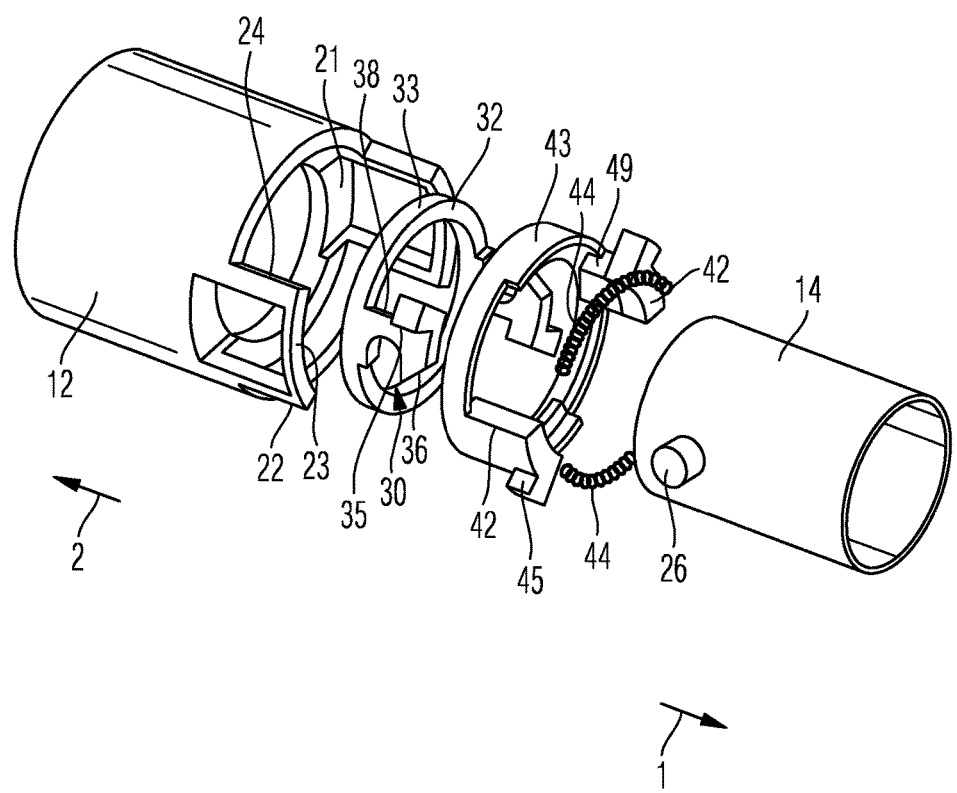
FIG. 2 shows an exploded view of the connector assembly.
Figure 3:
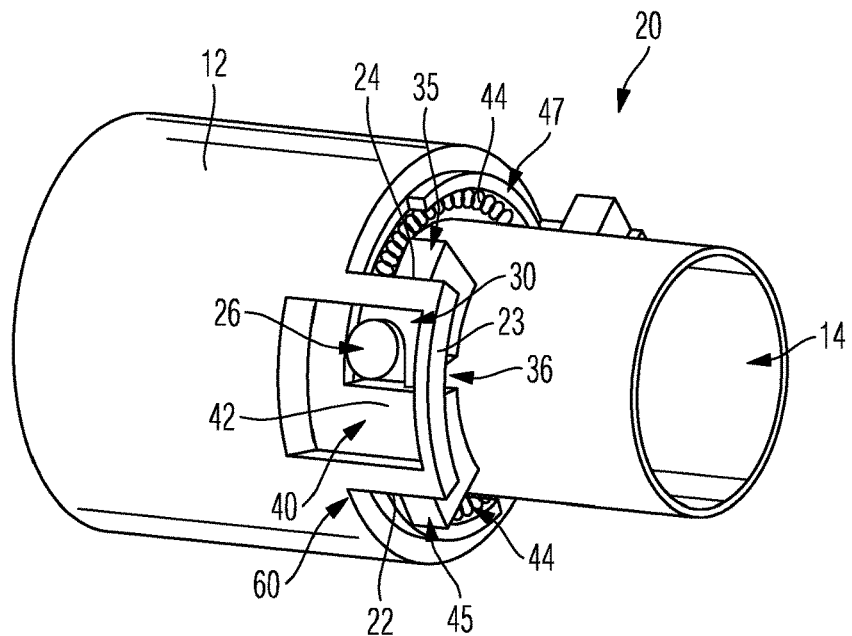
FIG. 3 shows a perspective illustration of the connector assembly in locking configuration.
Figure 4:
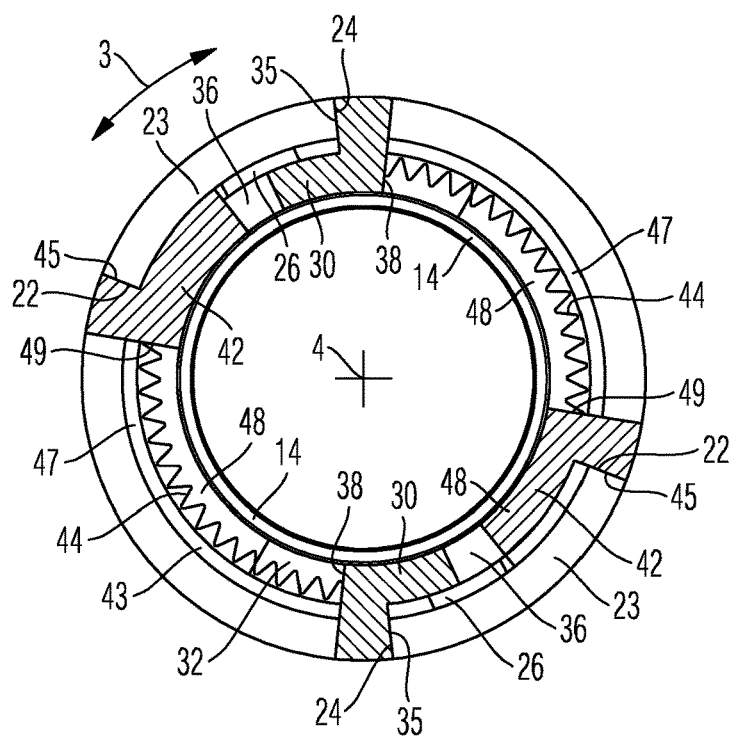
FIG. 4 is a front view of the connector assembly according to FIG. 3.
Figure 5:
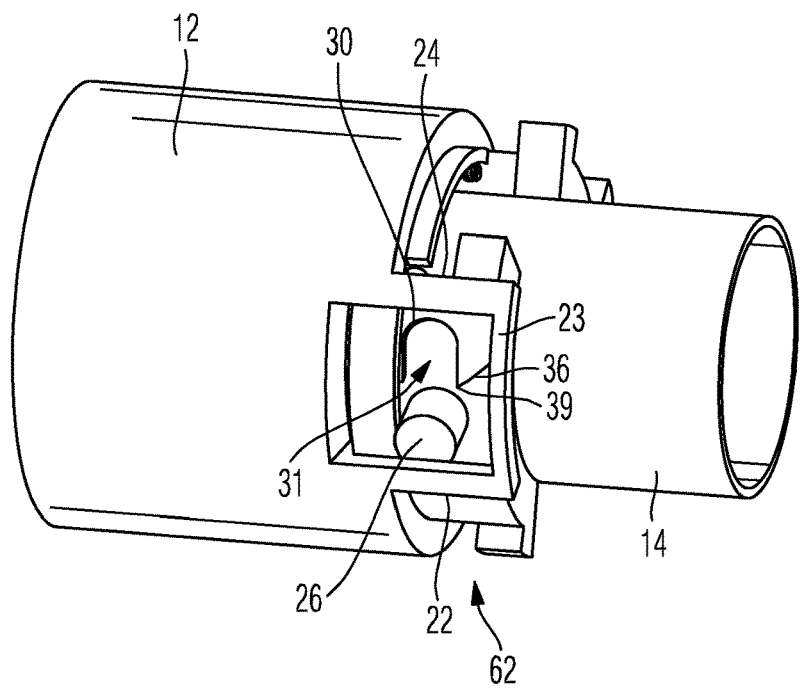
FIG. 5 shows a perspective view of the connector assembly in the release configuration.

The connector assembly 20 comprises a tangentially extending recessed structure 30 with a tangential opening 31 as shown in FIG. 5 that is designed to receive a radially extending pin 26. In the embodiment as shown in FIGS. 2-7 the tangentially extending recessed structure 30 belongs to a locking member 32 which is rotatably or pivotally attached to the body 12 and which is rotatable with respect to the longitudinal axis 4 as indicated in FIG. 4. The connector assembly 20 further comprises a release member 40 having a retaining portion 42 to cover, to close or to obstruct the opening 31 of the recessed structure 30 in a locking configuration which is illustrated in FIGS. 3 and 4. At least the release member 40 is rotatable or pivotable against a restoring force provided by return springs 44 in circumferential or tangential direction so as to separate from the recessed structure 30 and from the opening 31 in tangential direction and to allow removal of the pin 26 from the opening 31 and hence from the recessed structure 30.

The connector assembly 20 further comprises at least one pin 26 which is fastened to the outside-facing sidewall of the cartridge holder 14. In particular, the pin 26 may be integrally formed with the cartridge holder 14.

Even though the embodiment according to FIGS. 2-7 shows an arrangement with release member 40 and locking member 32 attached to the body and with pins 26 integrated into the cartridge holder 14 there are also other embodiments conceivable, where the pins 26 are located on the body 20 and wherein release member 40 and/or locking member 32 are rotatably supported on or in the cartridge holder 14.

Figure 6:
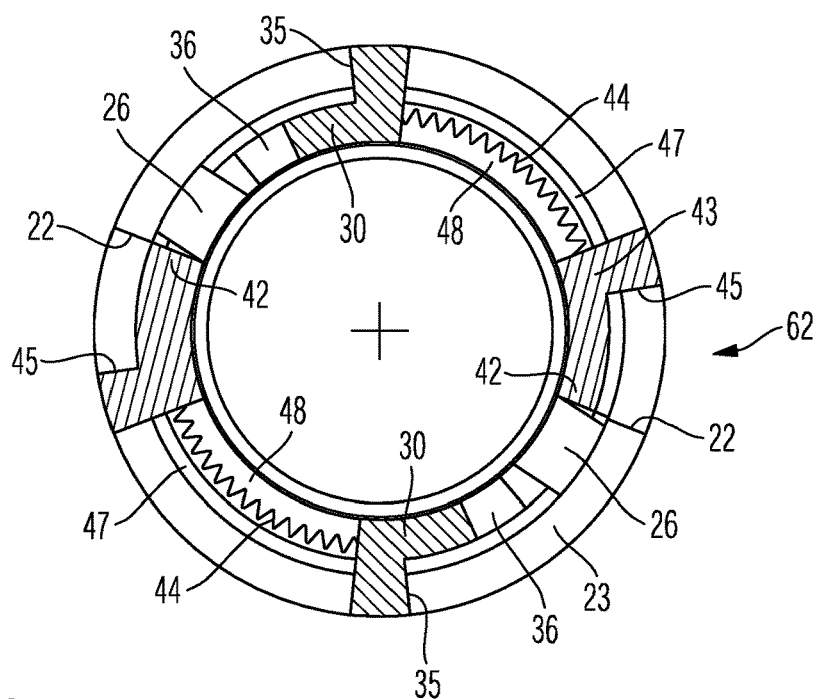
FIG. 6 is a front view of the connector assembly according to FIG. 5.
Figure 7:
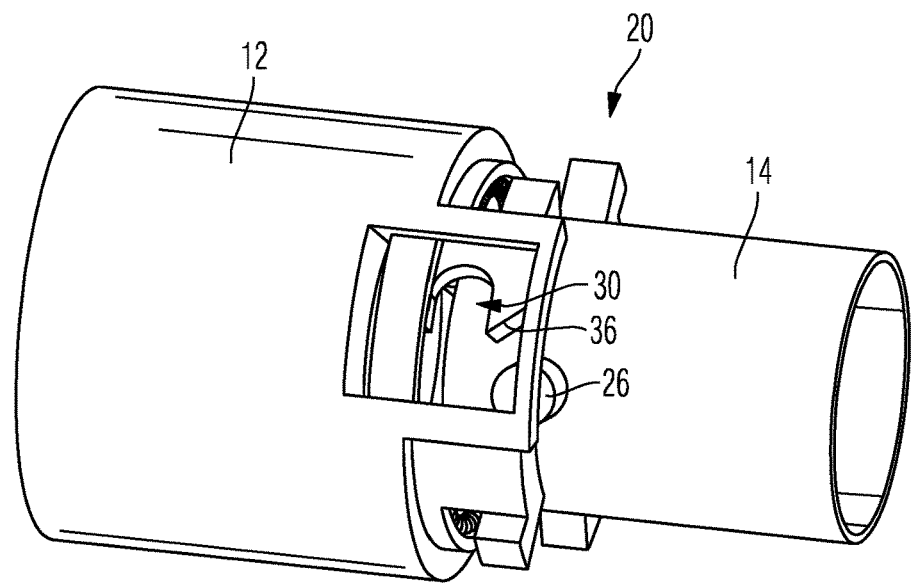
FIG. 7 shows the connector assembly during axial removal of the cartridge holder from the connector assembly and FIG. 8 schematically indicates an alternative embodiment of the connector assembly.

Both, the release member 40 as well as the locking member 32 comprise a ring structure 43, 33, respectively. As becomes apparent from FIG. 2, the locking member 32 is axially constrained or axially sandwiched between a bearing surface 21 of the body and the ring structure 43 of the release member 40. As illustrated in FIGS. 4 and 6 the release member 40, in particular its ring structure 43, comprises a radially inwardly extending flange portion 48 to radially overlap with the ring structure 33 of the locking member 32. Additionally, the release member 40 is axially fixed to the body 12, by some kind of fixing mechanism that serves to axially fix the release member 40 to the body 12 but which still supports and allows a rotation of the release member 40 relative to the body 12. In this way, also the locking member 32 is axially constrained or axially fixed to the body 12 but is free to rotate with regard to the longitudinal axis 4.

Release member 40 and locking member 32 are further engaged or coupled by means of two return springs 44, which are arranged geometrically opposite with respect to each other on and along the circumference of ring structures 33, 43 of the locking member 32 and the release member 40. The recessed structure 30 extends axially from the locking member's 32 ring structure 33. In the present embodiment as shown in FIG. 2 the recessed structure projects in distal direction from the circumference of the ring structure 33. A back face or backside 38 of the recessed structure 30 facing away from the tangentially directed opening 31 of the recessed structure may engage and abut with one end of a return spring 44 while an opposite end of the return spring 44 abuts with a front face 49 of a retaining portion 42 also extending in distal direction from the ring structure 43 of the release member 40.

In this way, the release member 40 and the locking member 32 are engaged and biased by the compressive return spring 44. As shown in the various FIGS. 2-7 the release member 40 comprises two geometrically opposed retaining portions 42 while the locking member 32 comprises two symmetrically-shaped and geometrically opposed recessed structures 30. As indicated in FIG. 4 opposite ends of the two return springs 44 engage and abut with tangentially or circumferentially neighboring back faces 38 and front faces 49 of recessed structures 30 and retaining portions 42 of locking members 32 and release members 40, respectively.

As seen from the front and when looking in proximal direction as indicated in FIG. 4, the release member 40 is rotatable counter-clockwise in a tangential direction 3 against the action of the return springs 44 while the locking member 32 is rotatable or pivotable with regards to the longitudinal axis 4 in a clockwise direction against the action of the return springs 44.

The action of the return springs 44 is counteracted or counterbalanced by means of radial stops. As shown in FIGS. 3 and 4 the release member 40 as well as the locking member 32 both comprise at least one radially outwardly extending stop to engage with a corresponding radial stop of the body. As shown in FIG. 3, the body comprises a radial stop 24 to abut with a correspondingly-shaped and radially outwardly extending radial stop 35 of the locking member 32. The radially outwardly extending radial stop 35 extends at a distal end of the recessed structure 30. Correspondingly, the distal free end of the retaining portion 42 of the release member 40 features a radially outwardly extending stop 45 which abuts and engages with another radial stop 22 of the body 12.

In the locking configuration as shown in FIGS. 3 and 4, the radial stops 35 and 45 of the locking member 32 and the release member 40 are both in direct abutment with corresponding radial stops 24, 22 of the housing 12. The radial stops 22, 24 of the body 12 extend in distal direction 1 from a sleeve-shaped distal end of the body 12. The free ends of the slab-shaped stops 22, 24 are interconnected by a ridge portion 23. In this way the radial stops 22, 24 can be mutually stabilized. Between the slab-like stops 22, 24 and the bridge portion 23 there is formed a kind of a window, which is shown here for illustration purpose mainly. In other embodiments it is conceivable, that the two radial stops 22, 24 are just provided by opposite ends of a closed shaped distally extending body portion.

In the locking configuration as shown in FIGS. 3 and 4 the two return springs 44 serve to keep the radial stops 35, 45 in abutment with corresponding radial stops 24, 22 of the body 12. As shown in FIG. 3, the pin 26 of the cartridge holder 14 is located and constrained in and by the recessed structure 30. Since the recessed structure 30 as well as the release member 40 are axially fixed to the body 12 the pins 26 of the cartridge holder and hence the cartridge 14 itself is axially fixed to the body 12.

As becomes further apparent from FIG. 3, the return springs 44 are circumferentially or tangentially guided by a rim 47 extending along the inside-facing sidewall portion of the body 12 and extending in distal direction from the radially inwardly directed flange portion 48 of the release member's 40 ring structure 43.

For transferring the connector assembly 20 from the locking configuration 60 as shown in FIGS. 3 and 4 into the release configuration 62 as shown in FIGS. 5 and 6, the cartridge holder 14 is to be rotated in tangential direction 3 counter-clockwise relative to the body 12. Due to this rotation the radially outwardly extending pins 26 transfer a respective counter-clockwise torque to the distally and axially extending retaining portions 42 of the release member 40. At the same time the pins 26 are tangentially removed from the recessed structure 30 and tangentially pass by an end portion 39 thereof. Due to the engagement of the radial stops 35 with the radial stops 24 the locking member 32 is unable to follow the tangential displacement of the pins 26. When reaching a configuration as illustrated in FIG. 5, wherein the pins have completely left the recessed structure 30, the cartridge holder 14 can be removed from the body 12 simply by tearing the cartridge holder 14 in distal direction relative to the body 12.

For reconnecting cartridge holder 14 and body 12 it is simply required to introduce the proximal end of the cartridge holder 14 into the cylindrical receptacle provided at the distal end of the body 12. As shown in FIGS. 2 and 5 the distal free end of the recessed structure 30, hence a distal end of the locking member 32 comprises a beveled edge 36. When the radially outwardly extending pins 26 of the cartridge holder 14 hit or engage the beveled edges 33 of the geometrically oppositely located recessed structures 30 of the locking member 32 a clockwise directed torque will be present on the locking member 32.

Assuming that the cartridge holder 14 is purely axially but non-rotatably guided relative to the body 12 the insertion of the cartridge holder 14 in proximal direction into the body 12 leads to a clockwise evasive movement of the locking member 32 until the pins 26 pass by the end portions 39 of the beveled edges 36. Since this evasive movement acts against the action of the return springs 44 the locking member 32 will return into the locking configuration 60 under the effect of the return springs 44 when the pins have axially passed by the tipped end portion 39 of the beveled edges 36.

Connecting or reconnecting of cartridge holder 14 and body 12 only requires to stick the cartridge holder 14 into the body in longitudinal direction. Releasing and disconnecting of cartridge holder 14 from the body 12 requires a tangential rotation of the cartridge holder 14 relative to the body 12 and a subsequent withdrawal of the cartridge holder 14 in distal direction from the body 12.

Figure 8:
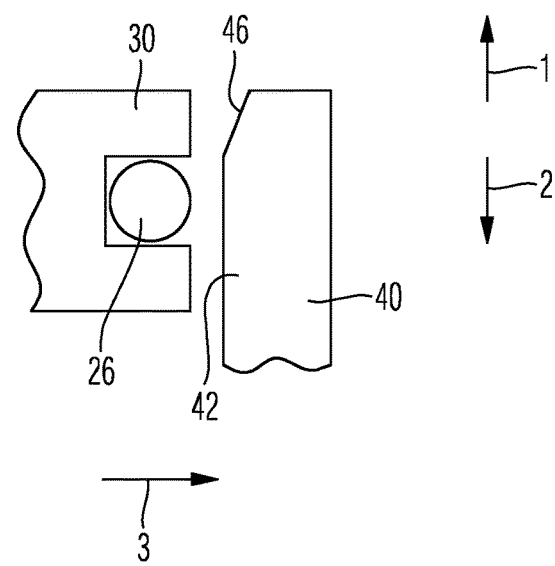

In FIG. 8 another embodiment is illustrated, wherein the recessed structure 30 may be integrally formed with the body 12 while the release member 40 is the only displaceable component engaged with a return spring 44. In contrast to the embodiment as illustrated in FIGS. 2-7 it is here the release member 40, which comprises a beveled edge 46 at a distal end towards the recessed structure 30. For inserting the pin 26 into the recessed structure 30, the pin 26 is equally urged in proximal direction 2 so as to induce an evasive movement of the release member's 40 retaining portion 42 away from the recessed structure 30. When having axially passed the beveled edge 46, the interior of the recessed structure 30 becomes accessible for the pin 26 in order to receive the same in a way as illustrated in FIG. 8. Since the pin 26 enters the recessed structure 30 in tangential direction 3 the release member 40 may then return into its locking configuration 60 as shown in FIG. 8.

The disconnecting of the embodiment according to FIG. 8 is almost equal to the disconnecting mechanism of the embodiment as described in connection with FIGS. 2-7.

REFERENCE NUMBERS 1 distal direction
2 proximal direction
3 tangential direction
4 longitudinal axis
5 drug delivery device
10 housing
11 cap
12 body
13 drive mechanism
14 cartridge holder
15 window
16 cartridge
17 actuation button
18 piston rod
19 dose selector
20 connector assembly
21 bearing surface
22 radial stop
23 bridge portion
24 radial stop
26 pin
30 recessed structure
31 opening
32 locking member
33 ring structure
35 radial stop
36 beveled edge
38 back face
39 end portion
40 release member
42 retaining portion
43 ring structure
44 return spring
45 radial stop 46 beveled edge
47 rim
48 flange portion
49 front face
60 locking configuration
62 release configuration

The invention claimed is:

1. A housing of a drug delivery device, the housing comprising:
a cylindrically shaped body to accommodate a drive mechanism;
a cartridge holder to accommodate a cartridge containing a dispensable medicament; and
a connector assembly to releasably interconnect the body and the cartridge holder, the connector assembly comprising:
a locking member comprising a tangentially extending recessed structure with an access opening facing in a tangential direction and configured to tangentially receive a radially extending pin, wherein the pin is insertable into the access opening in the tangential direction, wherein the locking member is fastened to one of the body or the cartridge holder and wherein the pin is fastened to the other one of the body or the cartridge holder, and
a release member having a retaining portion, wherein the release member is displaceable relative to the locking member from a locking configuration in the tangential direction against a restoring force away from the recessed structure into a release configuration, wherein when the release member is in the locking configuration, the retaining portion covers the access opening and when the release member is in the release configuration, the access opening is uncovered and enables the pin to be tangentially removed from the access opening.

2. The housing according to claim 1, wherein the release member is rotatably or pivotably supported on one of the body or the cartridge holder with respect to a longitudinal axis of the body or the cartridge holder.

3. The housing according to claim 1, wherein the release member comprises a ring structure and wherein the retaining portion axially protrudes from the ring structure.

4. The housing according to claim 1, wherein the release member comprises a radially extending radial stop to engage with a complementary radial stop of the body or the cartridge holder to delimit a tangential displacement of the release member towards the locking configuration.

5. The housing according to claim 1, wherein the release member is displaceable against an action of at least one tangentially extending return spring.

6. The housing according to claim 5, wherein the at least one return spring tangentially extends between the locking member and the release member to keep the retaining portion in abutment with the recessed structure.

7. The housing according to claim 1, wherein the locking member is rotatably or pivotably supported with respect to a longitudinal axis of the body or the cartridge holder on one of the body and the cartridge holder, the one of the body and the cartridge holder supporting the release member.

8. The housing according to claim 1, wherein the release member and the locking member axially abut and wherein one of the release member and the locking member is axially fixed to one of the body and the cartridge holder to axially constrain the other one of the release member and the locking member in abutment with a bearing surface of the one of the body and the cartridge holder.

9. The housing according to claim 1, wherein the locking member comprises a ring structure and wherein the recessed structure axially protrudes from the ring structure.

10. The housing according to claim 1, wherein the locking member comprises a radially extending radial stop to engage with a complementary radial stop of the body or the cartridge holder to delimit a locking member's tangential displacement towards the locking configuration.

11. The housing according to claim 1, wherein the release member comprises at least two tangentially separated retaining portions to releasably engage with at least two correspondingly shaped and separated recessed structures.

12. The housing according to claim 1, wherein a free and axial end of at least one of the recessed structure and the retaining portion comprises a beveled edge.

13. The housing according to claim 12, wherein the connector assembly is transferable from the locking configuration into the release configuration by a tangential displacement of the locking member relative to the release member induced by an axial displacement of the pin towards the release member thereby engaging with the beveled edge.

14. A drug delivery device comprising: a housing comprising:
a cylindrically shaped body;
a cartridge holder to accommodate a cartridge containing a dispensable medicament;
a connector assembly to releasably interconnect the body and the cartridge holder, the connector assembly comprising:
a locking member comprising a tangentially extending recessed structure with an access opening facing in a tangential direction and configured to tangentially receive a radially extending pin, wherein the pin is insertable into the access opening in the tangential direction, wherein the locking member is fastened to one of the body or the cartridge holder and wherein the pin is fastened to the other one of the body or the cartridge holder, and
a release member having a retaining portion, wherein the release member is displaceable relative to the locking member from a locking configuration in the tangential direction against a restoring force away from the recessed structure into a release configuration, wherein when the release member is in the locking configuration, the retaining portion covers the access opening and when the release member is in the release configuration, the access opening is uncovered and enables the pin to be tangentially removed from the access opening; and
a drive mechanism arranged in the body of the housing and comprising at least a piston rod to operably engage with a piston of a cartridge containing a medicament.

15. The drug delivery device according to claim 14, further comprising a replaceable cartridge filled with a medicament and being arranged in the cartridge holder.

16. The drug delivery device according to claim 14, wherein the medicament comprises at least one pharmaceutically active compound.

* * * * *